United States Patent
Zimmermann et al.

(10) Patent No.: US 6,387,280 B1
(45) Date of Patent: May 14, 2002

(54) PROCESS FOR REDUCING THE AMOUNT OF NITRIFICATION-INHIBITING SULFUR COMPOUNDS

(75) Inventors: Curt Zimmermann, Mauthausen; Helmut Sengstschmid, Linz; Willibald Scheuchenstuhl, Oswald/Freistadt, all of (AT)

(73) Assignee: DSM Fine Chemicals Austria Nfg GmbH & CoKG, Linz (AT)

( * ) Notice: Subject to any disclaimer, the term of this patent is extended or adjusted under 35 U.S.C. 154(b) by 0 days.

(21) Appl. No.: 09/717,349

(22) Filed: Nov. 22, 2000

(30) Foreign Application Priority Data

Nov. 22, 1999 (AT) ............................................. 1973/99

(51) Int. Cl.⁷ .................................................. C02F 1/72
(52) U.S. Cl. ........................ 210/758; 210/759; 210/760; 210/903; 210/908
(58) Field of Search ................................ 210/758, 759, 210/760, 903, 908

(56) References Cited

U.S. PATENT DOCUMENTS

| 4,416,786 A | 11/1983 | Knorre et al. |
| 5,169,532 A | * 12/1992 | Whitlock |
| 5,180,500 A | 1/1993 | McConnell |

FOREIGN PATENT DOCUMENTS

| BE | 871 436 | | 9/1979 |
| JP | 53-094445 | | 8/1978 |
| JP | 56-158192 | | 3/1982 |
| JP | 59-189996 | | 9/1984 |
| JP | 62-056446 | | 6/1987 |
| JP | 411033571 A | * | 2/1999 |
| SU | 1028-607 | | 6/1984 |
| SU | 1303-560 | | 7/1987 |

* cited by examiner

Primary Examiner—Betsey Morrison Hoey
(74) Attorney, Agent, or Firm—Wenderoth, Lind & Ponack, LLP

(57) ABSTRACT

A process for reducing the amount of nitrification-inhibiting sulfur compounds in reaction solutions obtained by the sulfur-compound-catalyzed conversion of $\alpha,\beta$-unsaturated carboxylic acids into the corresponding trans or cis isomer, in which an oxidizing agent is added in molar deficiency up to a maximum of twice the molar amount, based on the catalyst compound, to the reaction mixture obtained after the termination of the isomerization and then isolating the corresponding trans or cis isomer in a known manner and working it up and supplying the resultant process waste waters to a biological cleanup stage.

8 Claims, No Drawings

PROCESS FOR REDUCING THE AMOUNT OF NITRIFICATION-INHIBITING SULFUR COMPOUNDS

Process for reducing the amount of nitrification-inhibiting sulfur compounds.

The invention relates to a process by which the residual amount of nitrification-inhibiting sulfur compounds, which are used as isomerization catalyst in the conversion of α,β-unsaturated carboxylic acids into the corresponding trans or cis isomer is reduced to the extent that no nitrification inhibition occurs during cleanup in biological sewage treatment plants.

In industrial-scale processes, in principle the most varied types of waste occur, which must be disposed of without environmental pollution. A problem in the disposal of process waste waters is, inter alia, their pollution by sulfur compounds. Thiourea, for instance, has been classified by the U.S. Environmental Protection Agency as a hazardous substance. It is known to act as an inhibitor in the nitrification process in biological sewage treatment plants. Especially in the removal of nitrogen and phosphorus, the nitrification rate is limiting for the performance of biological sewage treatment plants. Such sewage treatment plants therefore react sensitively to specific inhibitors present in industrial waste waters. Since most sulfur compounds, however, also have nitrification-inhibiting activity, it is thus necessary to reduce the content of these compounds in the process waste waters before introduction into the biological effluent channel. For this purpose the nitrification-inhibiting compounds can either be completely removed or their content reduced at least to the extent that the conditions for environmentally tolerable disposal by the biological sewage treatment plants are fulfilled. Nitrification-inhibiting sulfur compounds in this case are, in addition to thiourea, sulfur compounds such as thioamide compounds, thiocyanates, thiazoles or thiosemicarbazides, which are widely used, inter alia, in the preparation and modification of synthetic resins, preparation of pharmaceuticals, industrial cleaning aids, use as antioxidant and as isomerization catalyst in the conversion of α,β-unsaturated carboxylic acids into the corresponding trans or cis isomer.

One method of disposal of waste waters polluted in this manner is incineration, thermal decomposition using NaOH at elevated temperature over a relatively long period (for example 4 days) or reaction with sodium hypochlorite. The disadvantages of these processes are, firstly, the complex exhaust gas emission control (denox and desulfurization) and additional costs caused as a result, and loss of time and, secondly, in the reaction with sodium hypochlorite, the formation of hazardous chlorinated organic compounds. As an improvement, U.S. Pat. No. 4,822,494 suggests a two-step process for removing thiourea from spent hydrochloric acid cleaning solutions, in which, in the first step an alkali metal hydroxide or alkaline earth metal hydroxide is added to the solution until a pH of at least 12 is reached and, in the second step, firstly at least 4 mol of hydrogen peroxide are added per mole of thiourea and then an alkali metal hypochlorite or alkaline earth metal hypochlorite is added, as a result of which the thiourea present is oxidized to urea, which is then completely decomposed. However, this process is rather complex and thus uneconomic.

The object of the present invention was therefore to find a simple process by which the amount of nitrification-inhibiting sulfur compounds which are used as isomerization catalyst in the conversion of α,β-unsaturated carboxylic acids into the corresponding trans or cis isomer is reduced to the extent that environmentally tolerable disposal of the process waste waters is ensured.

Unexpectedly, this object was achieved by simple addition of an oxidizing agent in molar deficiency up to a maximum of twice the molar amount to a solution or reaction solution polluted by nitrification-inhibiting sulfur compounds, which solution is obtained by conversion of α,β-unsaturated carboxylic acids into the corresponding trans or cis isomer, in which case the adjustment to a basic pH is avoided and the addition can take place before isolation of reaction products.

The present invention therefore relates to a process for reducing the amount of nitrification-inhibiting sulfur compounds in reaction solutions obtained by the sulfur-compound-catalyzed conversion of α,β-unsaturated carboxylic acids into the corresponding trans or cis isomer, which comprises adding an oxidizing agent in molar excess up to a maximum of twice the molar amount, based on the catalyst compound, to the reaction mixture obtained after the termination of the isomerization and then isolating the corresponding trans or cis isomer in a known manner and working it up and supplying the resultant process waste waters to a biological cleanup stage.

According to the invention, the amount of nitrification-inhibiting sulfur compound s in reaction solutions obtained by sulfur-compound-catalyzed conversion of α,β-unsaturated carboxylic acids into the corresponding trans or cis isomer is reduced, as a result of which the process waste waters produced in this reaction can be supplied to biological to without problem.

Nitrification-inhibiting sulfur compounds in this case are sulfur compounds such as thioamide compound, thiocyanates, thiazoles or thiosemicarbazides. Preference is given to thioamide compounds. Suitable thioamide compounds in this case are compounds of the formula

(I)

where

R is H, $C_1$–$C_{20}$-alkyl or alkenyl, benzyl, naphthyl or $NR_1R_2$;

$R_1$ and $R_2$ can be identical or different and are H or $C_1$–$C_{10}$-alkyl.

Alkyl radicals or alkenyl radicals in this case are radicals which can be unbranched, cyclic or branched, for instance methyl, ethyl, isopropyl, n-propyl, n-butyl, t-butyl, hexyl, dodecyl, cyclopentyl, cyclopentamethylene, etc. Examples of these are thioformamide, thioacetamide, thiopropionamide, thiobutyramide, thiovaleramide, thiododecylamide, thiobenzamide, thioaphthamide, thioacrylamide, thio-N-methylacetamide, thio-N,N-dimethylacetamide, thio-N,N-diethylacetamide, thio-N-cyclopentamethylenebenzamide, thiourea, etc.

Preferably, R is a radical $NR_1R_2$. Particularly preferably, R is a radical $NR_1R_2$ and $R_1$ and $R_2$ are each H. A particularly preferred thioamide compound is therefore thiourea.

The inventive process is used in the conversion of unsaturated compounds, for instance α,β-unsaturated carboxylic acids, into the corresponding trans or cis isomer. Preferably, the inventive process is used in the conversion of maleic acid to fumaric acid.

In the workup of the reaction solutions obtained via the abovementioned processes, for example in the isolation by filtration of a trans isomer from the reaction mixture which is polluted by the sulfur compound used as catalyst, these nitrification-inhibiting sulfur compounds pass into the process waste water, for example via the mother liquor separated off.

To reduce the amount of nitrification-inhibiting sulfur compounds, a suitable oxidizing agent is added to the reaction mixture or solution obtained via one of the above mentioned processes. The addition is preferably performed directly after the reaction is complete, but before the actual workup of the reaction solution. Thus, for example, in the preparation of fumaric acid from maleic acid, the oxidizing agent is added to the reaction solution directly after completion of the isomerization, but still before the isolation of fumaric acid. Unexpectedly, no adverse effects on the course of the reaction or product quality occur in this case. In addition, it is unnecessary to make the reaction solution alkaline and/or to change the temperature of the respective reaction mixture.

If appropriate, however, the addition can also be performed after workup of the reaction solution until shortly before the biological cleanup of the process waste water.

The temperature of the addition of the oxidizing agent can thus, depending on the time of the addition, be between room temperature and the reaction temperature of the corresponding process, with higher temperatures beneficially affecting the reaction kinetics.

Suitable oxidizing agents are, for example, ozone, inorganic soluble persulfates, hydrogen peroxide, organic peroxides and hydroperoxides, peracids, for instance ammonium persulfate, sodium persulfate, potassium persulfate, lithium persulfate, calcium persulfate, magnesium persulfate, benzoyl peroxide, cyclohexanone peroxide, acetyl peroxide, lauroyl peroxide, t-butyl peroxide, t-butyl hydroperoxide, etc.

Preferably, hydrogen peroxide or inorganic persulfates, particularly preferably hydrogen peroxide, are used as oxidizing agent.

The amount of added oxidizing agent depends on the desired degree of reduction of nitrification inhibition in the process waste water. The nitrification inhibition which is tolerated in the process waste water can vary from country to country. Depending on the stipulations for the sewage treatment plants which clean up the process waste waters, it is sometimes sufficient alternatively to reduce the amount of nitrification-inhibiting sulfur compounds only to the extent that, although complete elimination of nitrification inhibition is not achieved, peak values which are no longer tolerated are correspondingly lowered.

For this reason, the oxidizing agent, depending on the desired degree of reduction of the residual amount of nitrification-inhibiting sulfur compounds, is added in a molar deficiency up to twice the molar amount with respect to nitrification-inhibiting sulfur compounds. Preferably, the oxidizing agent is added in an amount of from 0.1 mol to 1 mol per mole of nitrification-inhibiting sulfur compounds.

By adding the oxidizing agent the nitrification-inhibiting sulfur compounds are oxidized to the extent that the inhibition of the nitrification process in biological sewage treatment plants is sufficiently to completely eliminated.

Particularly preferably, the process is employed in the preparation of fumaric acid from maleic acid using thioamide compounds of the formula (I) as isomerization catalyst. Among the thioamide compounds of formula (I), in turn thiourea is particularly preferred.

The oxidizing agent, preferably hydrogen peroxide or inorganic persulfates, particularly preferably hydrogen peroxide, is added to the reaction mixture, preferably directly after completion of the isomerization reaction, and the reaction mixture is stirred.

The temperature at the addition is preferably the isomerization temperature, that is to say about 80–90° C. If appropriate, the reaction mixture can also have been cooled, however, prior to addition of the oxidizing agent. The preferred amount of oxidizing agent is from 0.1 to 1 mol per mole of catalyst compound.

The stirring time depends on the temperature at the addition and is preferably 1–120 minutes, particularly preferably between 10 and 30 minutes.

However, it is also possible not to add the oxidizing agent until later, after removal of the trans isomer, directly to the process waste water. The addition can be made up to shortly before workup of the process waste waters in the sewage treatment plant.

By means of the inventive process, in a simple and economic manner a reduction in the residual amount of nitrification-inhibiting sulfur compounds is achieved in the waste water to the preset value. The direct addition of the oxidizing agent to the respective reaction mixtures or solutions in this case has no adverse effects either on the course of the reaction or on the product quality.

EXAMPLE 1

Standard 220 g (1.9 mol) of maleic acid in the form of a 20% strength (g/g) aqueous solution, which has been produced as scrubbing water in the course of phthalic anhydride production was placed in a reaction vessel equipped with stirrer, heating, thermometer and reflux condenser. In addition to maleic acid, the solution also contained 1% (g/g) of benzoic acid, 1.4% (g/g) of phthalic acid and small amounts of solid and dissolved tar-like constituents which were not studied further. The fumaric acid content was below 0.2%. The nitrification inhibition of the maleic solution was measured in the conventional manner by preparing a dilution series as specified in DIN EN 29888. The result of the measurement reports the sample dilution at which a defined inhibitory threshold (EC20) is no longer exceeded in the degradation test. For the maleic acid solution used, a value of 1:260 (EC20) was found. After heating to 90° C., 7.9 g (104 mmol) of thiourea in the form of a 33% strength (g/g) hot aqueous solution were added and stirred for 2 h at 90° C. The resultant suspension was cooled and filtered. Determination of the nitrification inhibition of the filtrate gave a value of 1:9110 (EC20). The filter cake was dissolved in boiling water, activated carbon and filter aid were added and the mixture was filtered hot. The filtrate was cooled and the resultant precipitate was filtered. After drying the filter cake, 192 g (1.653 mol) of fumaric acid were obtained (yield 87%).

EXAMPLE 2

Substoichiometric $H_2O_2$ Treatment

In a similar manner to example 1, 220 g (1.9 mol) maleic acid in the form of a 20% strength (g/g) aqueous solution was heated to 90° C. As in the preceding example, 7.9 g (104 mmol) of thiourea were added in the form of a 33% strength (g/g) hot aqueous solution and the mixture was stirred for 2 h at 90° C. 5.9 g of 30% strength (g/g) hydrogen peroxide (52 mmol) were then added. After stirring for a further 15 min, a negative peroxide test indicated that the hydrogen peroxide had reacted completely with thiourea. The reaction solution was filtered and the nitrification inhibition of the filtrate was determined in a similar manner to example 1. A value of 1:3450 (EC20) was measured. The filter cake was worked up as in example 1. No differences from example 1 were found either in the yield (192 g) or in the quality of the fumaric acid (HPLC analysis and peroxide test).

EXAMPLE 3

Stoichiometric $H_2O_2$ Treatment

In a similar manner to example 1, 220 g (1.9 mol) of maleic acid in the form of a 20% strength (g/g) aqueous solution were heated to 90° C. 7.9 g (104 mmol) of thiourea in the form of a 33% strength (g/g) hot aqueous solution were then added and the mixture was stirred at 2 h for 90° C. After addition of 11.8 g of 30% strength (g/g) hydrogen peroxide (104 mmol of $H_2O_2$) and stirring for a further 15 min, a negative peroxide test indicated that the hydrogen peroxide had reacted completely with thiourea. The reaction solution was filtered and the nitrification inhibition of the filtrate was determined as in example 1. A value of 1:680 (EC20) was found. The filter cake was worked up in a similar manner to example 1. No differences from example 1 were found either in the yield (192 g) or in the quality of the fumaric acid (HPLC analysis and peroxide test).

What is claimed is:

1. A process for reducing the amount of nitrification-inhibiting sulfur compounds in reaction solutions obtained by the sulfur-compound-catalyzed conversion of $\alpha,\beta$-unsaturated carboxylic acids into the corresponding trans or cis isomer, which comprises adding an oxidizing agent in molar deficiency up to a maximum of twice the molar amount, based on the nitrification-inhibiting sulfur compound, to the reaction mixture obtained after the termination of the isomerization and then isolating the corresponding trans or cis isomer and supplying the resultant process waste waters to a biological cleanup stage.

2. The process as claimed in claim 1, wherein the nitrification-inhibiting sulfur compound present in the reaction solution is a compound selected from the group consisting of thioamide compounds, thiocyanates, thiazoles and thiosemicarbazides.

3. The process as claimed in claim 2, wherein the nitrification-inhibiting sulfur compounds present are thioamide compounds of the formula

(I)

where R is H, $C_1-C_{20}$-alkyl or alkenyl, benzyl, naphthyl or $NR_1R_2$; $R_1$ and $R_2$ can be identical or different and are H or $C_1-C_{10}$-alkyl.

4. The process as claimed in claim 1, wherein the oxidizing agent used is ozone, inorganic soluble persulfates, hydrogen peroxide, organic peroxides and hydroperoxides or peracids.

5. The process as claimed in claim 4, wherein the oxidizing agent used is hydrogen peroxide or inorganic persulfates.

6. The process as claimed in claim 1, wherein the sulfur-compound-catalyzed conversion of cis-$\alpha,\beta$-unsaturated carboxylic acids into the corresponding trans isomer relates to the preparation of fumaric acid from maleic acid using thioamide compounds of the formula

(I)

where R is H, $C_1-C_{20}$-alkyl or alkenyl, benzyl, naphthyl or $NR_1R_2$; $R_1$ and $R_2$ can be identical or different and are H or $C_1-C_{10}$-alkyl, as isomerization catalyst.

7. The process as claimed in claim 1, wherein the oxidizing agent is used in an amount of from 0.1 to 1 mol per mole of nitrification-inhibiting sulfur compounds.

8. The process as claimed in claim 1, wherein the oxidizing agent is added to the reaction mixture at the isomerization temperature directly after termination of the isomerization reaction, the reaction mixture is stirred and then the trans or cis isomer is isolated from the reaction mixture.

* * * * *